United States Patent
Portoghese

(10) Patent No.: US 6,271,239 B1
(45) Date of Patent: Aug. 7, 2001

(54) DELTA OPIOID RECEPTOR-SELECTIVE BENZYLIDENE-SUBSTITUTED MORPHINANS

(75) Inventor: Philip S. Portoghese, St. Paul, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 0 days.

(21) Appl. No.: 08/440,989

(22) Filed: May 15, 1995

Related U.S. Application Data

(62) Division of application No. 07/867,997, filed on Apr. 13, 1992, now abandoned, which is a continuation of application No. 08/267,844, filed on Jun. 29, 1994, now abandoned.

(51) Int. Cl.$^7$ .................................................. A61K 31/439
(52) U.S. Cl. ........................................................... 514/282
(58) Field of Search .............................................. 514/282

(56) References Cited

U.S. PATENT DOCUMENTS

| | | | |
|---|---|---|---|
| 4,816,586 | * | 3/1989 | Portoghese ............................. 546/31 |
| 5,086,058 | * | 2/1992 | Sinclair et al. ...................... 514/282 |
| 5,352,680 | * | 10/1994 | Portoghese et al. ................. 514/282 |
| 5,464,841 | * | 11/1995 | Portoghese et al. ................. 514/279 |

OTHER PUBLICATIONS

Stillson et al., Jour. Am. Chem Soc. vol. 67 pp. 303–307 (1945).*
Portoghese et al., Jour Med Chem vol. 34, pp. 1292–1296 (Apr. 1991).*

* cited by examiner

*Primary Examiner*—Richard L. Raymond
(74) *Attorney, Agent, or Firm*—Schwegman, Lundberg, Woessner & Kluth, P.A.

(57) ABSTRACT

A delta-selective opioid receptor antagonist is provided of the formula:

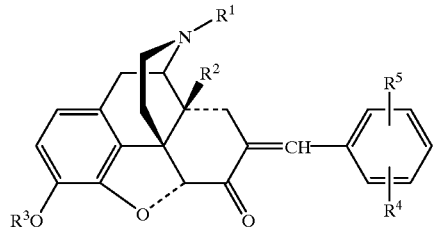

wherein $R^1$ is ($C_1$–$C_3$)alkyl, $C_3$–$C_6$(cycloalkyl)alkyl, $C_5$–$C_7$(cycloalkenyl)alkyl, aryl, aralkyl, trans-($C_4$–$C_5$)alkenyl, allyl or furan-2-ylalkyl, $R^2$ is H, OH or $O_2C(C_1$–$C_5)$alkyl; $R^3$ is H, ($C_1$–$C_5$)alkyl; or (($C_1$–$C_5$)alkyl)-C=O; and $R^4$ and $R^5$ are individually H, F, Cl, Br, $NH_2$, $NO_2$, ($C_1$–$C_5$)alkyl or ($C_1$–$C_5$)alkoxy, or $R^4$ and $R^5$ together are benzo or dioxymethylene; and the pharmaceutically acceptable salts thereof.

1 Claim, No Drawings

DELTA OPIOID RECEPTOR-SELECTIVE BENZYLIDENE-SUBSTITUTED MORPHINANS

This is a division, of application Ser. No. 08/267,844, filed Jun. 29, 1994, now abandoned which is a continuation of application Ser. No. 07/867,997, filed Apr. 13, 1992 now abandoned.

This invention was made with the assistance of the Government under a grant from the Public Health Service (Grant No. DA 01533). The U.S. Government has certain rights in the invention.

BACKGROUND OF THE INVENTION

The use of aldehyde dehydrogenase (ALDH) inhibitors is one pharmacotherapeutic approach which has been employed for the treatment of alcohol (ethanol) abuse and alcoholism. Examples of these types of compounds presently used clinically are disulfiram (tetraethylthiuram disulfide) (Antabuse®), and carbimide (citrated calcium carbimide, cyanamide (Temposil®)). Disulfiram is used through-out the world, whereas calcium carbimide has not been approved by the FDA for use in the United States.

The rationale for the use of ALDH inhibitors such as disulfiram for the treatment of alcoholism is that they block the metabolism of ethanol. Thus, after ethanol ingestion, inhibitors of liver mitochondrial low Km ALDH cause an increase in the formation of acetaldehyde. Clinically, this leads to tachycardia, hypotension, nausea, and other adverse symptoms that are referred to as the disulfiram-ethanol reaction (DER). Although disulfiram is widely used in the treatment of alcoholism, its use is not without controversy. A number of reports have questioned disulfiram's toxicity and its ability to produce a DER that is effective to deter ethanol ingestion.

Endogenous opioid peptides are involved in the mediation or modulation of a variety of mammalian physiological processes, many of which are mimicked by opiates or other non-endogenous opioid ligands. Some of the effects that have been investigated are analgesia, tolerance and dependence, appetite, renal function, gastrointestinal motility, gastric secretion, learning and memory, mental illness, epileptic seizures and other neurological disorders, cardiovascular responses, and respiratory depression.

The fact that the effects of endogenous and exogenous opioids are mediated by at least three different types [mu ($\mu$), delta ($\delta$), kappa ($\kappa$)] of opioid receptors raises the possibility that highly selective exogenous opioid agonist or antagonist ligands might have therapeutic applications. See W. R. Martin, *Pharmacol. Rev.*, 35, 283 (1983). Thus, if a ligand acts at a single opioid receptor type or subtype, the potential side effects mediated through other opioid receptor types can be minimized or eliminated.

The prototypical opioid antagonists, naloxone and naltrexone, are used primarily as pharmacologic research tools and for the reversal of toxic effects of opioids in case of overdose. Since these antagonists act at multiple opioid receptors, their application in other therapeutic areas or as pharmacologic tools appear to be limited. However, naltrexone recently was reported to reduce the incidence of relapse in recovering alcoholics by J. R. Volpicelli et al., *Opioids, Bulimia and Alcohol Abuse and Alcoholism*, L. D. Reid, ed., Springer-Verlag (1990) at pages 195–214. Naloxone has been reported to suppress ethanol but not water intake in a rat model of alcoholism. J. C. Froehlich et al., *Pharm. Biochem. Behav.*, 35, 385 (1990).

Some progress has been made in the development of highly selective opioid antagonists. For example, Portoghese et al. (U.S. Pat. No. 4,816,586) disclose certain opiate analogs which possess high selectivity and potency at delta receptors. Minimal involvement was observed at mu and kappa opioid receptors. One of the highly selective analogs disclosed in U.S. Pat. No. 4,816,586 has been named "naltrindole" or "NTI," and has the formula:

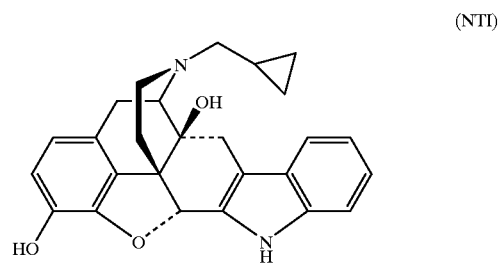

(NTI)

See P. S. Portoghese et al., *J. Med. Chem.*, 31, 281 (1988).

It has recently been reported that suppression of ethanol ingestion may be mediated by the delta opioid receptor type. For example, the established $\delta$ antagonist, N,N-diallyl-Tyr-Aib-Aib-Phe-Leu-OH (ICI 174864), strongly inhibits ethanol drinking, but has a very short duration of action, which may limit its clinical utility. See J. C. Froehlich et al., *Psychopharmacol.*, 103, 467 (1991). Using NTI as an antagonist, M. Sofuoglu et al., *J. Pharmacol. Exp. Ther.*, 257, 676 (1991) determined that the antinociceptive activity of two delta receptor agonist enkephalin analogs, DSLET and DPDPE, may be mediated by two discrete delta opioid receptor subtypes.

Therefore, a continuing need exists for compounds which are $\delta$ opioid receptor-selective. Delta opioid receptor antagonists are needed to develop pharmacological approaches to the treatment of alcohol dependence. More specifically, a need exists for an effective method to deter ethanol ingestion by humans using specific and potent $\delta$ opioid receptor antagonists, which have a duration of action and ability to access the central nervous system which are superior to the peptide-based $\delta$ receptor antagonists.

SUMMARY OF THE INVENTION

The present invention is directed to biologically active compounds of the formula I:

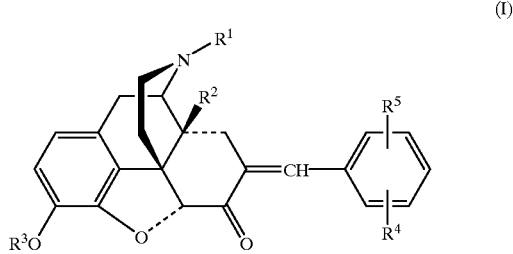

(I)

wherein $R^1$ is ($C_1$–$C_5$)alkyl, $C_3$–$C_6$(cycloalkyl)alkyl, $C_5$–$C_7$-(cycloalkenyl)alkyl, aryl, aralkyl, trans($C_4$–$C_5$) alkenyl, allyl or furan-2-ylalkyl, $R^2$ is H, OH or $O_2C(C_1$–$C_5)$ alkyl; $R^3$ is H, ($C_1$–$C_5$)alkyl or ($C_1$–$C_5$)alkylCO; and $R^4$ and $R^5$ are individually H, F, Cl, Br, $NO_2$, $NH_2$, ($C_1$–$C_5$)alkyl, ($C_1$–$C_5$)-alkoxy or together are dioxymethylene (—$OCH_2O$—) or benzo; and the pharmaceutically acceptable salts thereof.

The present invention also provides a method for blocking delta-opioid receptors in mammalian tissue comprising contacting said receptors in vivo or in vitro with an effective amount of the compound of formula I. Using peptide antagonists of known binding selectivity as standards, it was unexpectedly found that the compounds of the invention are selective for the $\epsilon_1$ subset of delta receptors. Thus, the compounds of formula I can be used as pharmacological and biochemical probes of opiate receptor structure and function, e.g., to measure the selectivity of other opioid receptor antagonists or agonists.

The present invention also can provide a method for suppressing ethanol ingestion by a human comprising administering to said human a pharmaceutical unit dosage form comprising an amount of a compound of the formula I. It is believed that compounds of formula I can decrease ethanol consumption by mammals without decreasing the intake of food or water for prolonged periods of time. Therefore, it is believed that the compounds of formula I will be clinically useful in the treatment of alcoholism, e.g., that they will be effective to decrease remission rates in recovering alcoholics. Also, the compounds of formula I may be co-administered with morphine to block its addictive effects without blocking its analgesic effects.

The alkyl moiety present in the $R^1$ group which links the cycloalkyl, cycloalkenyl, aryl, or furan-2-yl moiety to the basic nitrogen atom in the compounds of formula I is a lower(alkyl) group, preferably $-(CH_2)_n-$, wherein n is about 1–5, most preferably n is 1, e.g., $R^1$ is $C_3$–$C_6$(cycloalkyl)methyl, $C_5$–$C_7$(cycloalkenyl)methyl, arylmethyl or furan-2-yl-methyl. Preferred aryl moieties include ($C_6$–$C_{10}$)aryl, i.e., phenyl, benzyl, tolyl, napthyl, xylyl, anisyl and the like.

In formula I, the position of the $-R^4$ and $-R^5$ groups indicate that they can be either ortho, meta, or para to the =CH— group, e.g., $R^4$ and/or $R^5$ can occupy any available site on the phenyl ring. In structure I, a bond designated by a wedged or darkened line indicates one extending above the plane of the $R^3O$-substituted phenyl ring. A bond designated by a broken line indicates one extending below the plane of the phenyl ring.

Preferred delta-opioid antagonists include compounds of the formula I, wherein $R^1$ is ($C_1$–$C_5$)alkyl, $C_3$–$C_6$-(cycloalkyl)alkyl or $C_5$–$C_7$(cycloalkenyl)alkyl, preferably wherein $R^1$ is $C_3$–$C_6$(cycloalkyl)methyl, and most preferably wherein $R^1$ is cyclopropylmethyl. $R^2$ is preferably OH or OAc ($O_2CCH_3$), and $R^3$ preferably is H. Preferably, at least one, and most preferably, both of $R^4$ and $R^5$ are H. Preferred compounds also result when $R^4$ is H and $R^5$ is F, ($C_1$–$C_5$)alkyl or ($C_1$–$C_5$)alkoxy. The methylene-dioxy group is preferably a 3,4-methylene-dioxy group.

Since the compounds of the invention are formally morphinan derivatives, it is believed that their ability to cross the "blood-brain barrier" and to affect the central nervous system (CNS) should be far superior to peptide delta opioid antagonists. For example, as disclosed in U.S. patent application Ser. No. 07/750,109, filed Aug. 26, 1991, both NTI and its benzofuran analog, NTB produce unexpectedly prolonged suppression of ethanol drinking without altering water intake in rats that have been selectively bred for high voluntary ethanol drinking.

Therefore, the present invention is directed to a method to decrease ethanol intake by a mammal, such as a human afflicted with alcoholism or alcohol addiction, by administering an amount of a compound or formula I that is effective to block delta-opioid receptors, preferably $\delta_1$ opioid receptors, in mammalian tissue.

DETAILED DESCRIPTION OF THE INVENTION

The compounds of formula I can be readily synthesized by reacting a compound of formula II with benzaldehyde or a mono- or di-substituted derivative thereof in the presence of base, as shown below.

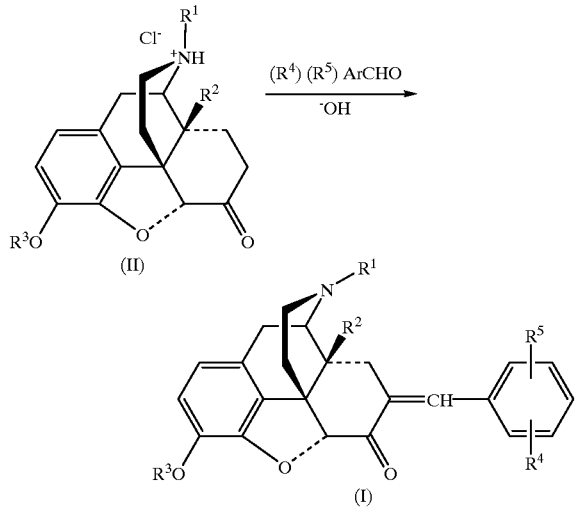

wherein $R^1$, $R^2$, $R^3$, $R^4$ and $R^5$ are as disclosed hereinabove. Preferably, II is naltrexone hydrochloride, e.g., $R^3$=H, $R^2$=OH and $R^1$=cyclopropylmethyl, and the synthesis of compound I wherein $R^2$=OH, $R^1$=cyclopropylinethyl and $R^3$=$R^4$=$R^5$=H is carried out as described by P. S. Portoghese et al., *J. Med. Chem.*, 34, 1292 (1991). When $OR^3$ and/or $R^2$ are base-liable groups such as alkanoxy, $R^3$ may be H and $R^2$ may be OH in the compound of formula I. In such situations, the protecting groups can be replaced by art-recognized methodologies for the protection/deprotection of hydroxyl groups. Of course, if naltrexone.HCl or a similar compound of formula II, comprising free OH groups is used to prepare compounds of formula I wherein $R^3$ is H and/or $R^2$ is OH or H, the free hydroxyl groups in the compound of formula I can be also converted to alkanoyloxy groups by methods known to the art.

The structures, common names and Merck Index reference numbers of representative 4,5-epoxy-6-keto-morphinan starting materials of general formula (II) are summarized on Table I, below.

TABLE I

10

| $R^1$ | $R^2$ | $R^3$ | Common Name | Merck No.[2] |
|---|---|---|---|---|
| $CH_2CH(CH_2)_2$ | OH | H | naltrexone | 6209 |
| $CH_3$ | OH | H | oxymorphone | 6837 |
| $CH_3$ | H | H | hydromorphone | 4714 |
| $CH_3$ | H | $CH_3$ | hydrocodone | 4687 |
| $CH_2CH(CH_2)_2$ | H | H | — | — |

TABLE I-continued

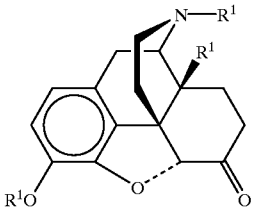

| R¹ | R² | R³ | Common Name | Merck No.[2] |
|---|---|---|---|---|
| CH₂CH=CH₂ | OH | H | naloxone | 6208 |
| CH₃ | OH | CH₃ | oxycodone | 6827 |

[1]Preparation, M. Gates et al., J. Med. Chem., 7, 127 (1964).
[2]The Merck Index, W. Windholz, ed., Merck & Co., Rahwav, NJ (10th ed. 1983).

Other starting materials of formula II can be prepared by synthetic methods which are well known in the art of organic chemistry. For example, compounds of formula II wherein $R^1$ is H and $R^3$ is a suitable protecting group, and wherein the 6-keto group has also been protected, can be prepared from compounds 10a–q. These intermediates can be N-alkylated and deprotected to yield compounds of formula I wherein $R^1$ is $C_2$–$C_5$(alkyl), $C_1$–$C_6$(cyclo-alkyl)alkyl, $C_5$–$C_7$(cycloalkenyl)alkyl, aryl, aralkyl, trans-$C_4$–$C_5$-alkenyl or furan-2-ylakyl, by the application of well known reactions.

For example, the free hydroxyl groups of compounds of formula II, e.g., $R^2$=OH and/or $R^3$=H, can be protected by acid-labile groups such as tetrahydropyranl-yl, trimethyl-silyl, 1-methoxy-isopropyl and the like as disclosed in *Compendium of Organic Synthetic Methods*, I. T. Harrison et al., eds., Wiley-Interscience, New York, N.Y. (1971) at pages 124–131, (hereinafter "Compendium"). The protection of the 6-keto group of compounds of formula 10 by its reversible conversion into a ketal or a thioketal group is disclosed in *Compendium*, at pages 449–453. Methods for the demethylation of N-methyl amines have been disclosed, for example, in *Compendium* at page 247, *J. Amer. Chem. Soc.*, 89, 1942 (1967) and *J. Amer. Chem. Soc.*, 77, 4079 (1955).

Procedures for the alkylation of secondary amines with halides under basic or neutral conditions are well known. For example, see *Compendium* at pages 242–245; *Org. Synth.*, 43, 45 (1963); *J. Org. Chem.*, 27, 3639 (1962) and *J. Amer. Chem. Soc.*, 82, 6163 (1960).

Compounds of formula II wherein $R^2$ is acyloxy and/or $R^3$is acyl can be prepared by using the corresponding starting materials on Table I. For example, naltrexone can be diacylated by reacting it with the appropriate ($C_1$–$C_5$)alkyl anhydride for 10–18 hrs at 18–25° C. The resultant 3,14-diacylated compound can be converted to the 14-acylated compound by limited hydrolysis. The 3-acylated starting materials can be prepared by the short-term reaction of the compounds of Table I with the anhydride, e.g., for about 2–4 hours. The 3-acylated product can be separated from the 3,14-diacylated product by chromatography.

The acid salts of compounds of formula I, wherein $R^3$=H, can be converted into the corresponding ($C_1$–$C_5$)alkoxy derivatives [$R^3$=($C_1$–$C_5$)alkyl] by dissolving the starting material in DMF and adding an excess of the appropriate ($C_1$–$C_5$)alkyl iodide and an amine such as diisopropylethylamine. The reaction can be conducted at an elevated temperature for about 4–10 hours. The final product can be purified by column chromatography.

The invention also comprises the pharmaceutically acceptable salts of the biologically active compounds of formula I, together with a pharmaceutically acceptable carrier for administration in effective, non-toxic dose form. Pharmaceutically acceptable amine salts may be salts of organic acids, such as acetic, citric, lactic, malic, tartaric, p-toluene sulfonic acid, methane sulfonic acid, and the like as well as salts of pharmaceutically acceptable mineral acids such as phosphoric, hydrochloric or sulfuric acid, and the like.

These physiologically acceptable salts are prepared by methods known in the art, e.g., by dissolving the free amine bases with an excess of the acid in aqueous alcohol.

In the clinical practice of the present method, the compounds of the present invention will normally be administered orally or parenterally, as by injection or infusion, in the form of a pharmaceutical preparation comprising the active ingredient in combination with a pharmaceutically acceptable carrier which may be a solid, semi-solid or liquid diluent or an ingestible capsule. The compound or its salt may also be used without carrier material. As examples of pharmaceutical carriers may be mentioned tablets, intravenous solutions, suspensions, microcapsules, liposomes and the like. Usually, the active substance will comprise between about 0.05 and 99%, or between 0.1 and 95% by weight of the resulting pharmaceutical unit dosage form, for example, between about 0.5 and 20% of preparation intended for injection or infusion and between 0.1 and 50% of preparation, such as tablets or capsules, intended for oral administration.

Since naltrexone has been evaluated clinically to assess its ability to inhibit ethanol consumption by alcoholic patients undergoing outpatient treatment, effective dosages of the compounds of the present invention can be extrapolated from doses found to be effective in that study, as well as from the dosages of NTI found to be effective to decrease ethanol consumption in the rat model.

The present compounds are believed to be able to suppress ethanol ingestion for a prolonged period of time, following administration of a single dose, e.g., by administration of a single unit dosage form. As used herein, the term "suppression" is intended to mean that the alcohol-addicted human or other subject will either abstain entirely from ethanol ingestion for a period of time following administration of a dose of the present compounds, or will ingest substantially less, e.g., at least about 15–50% less, of his or her baseline ethanol intake, i.e., before recovery. Preferably, administration of the present compounds can suppress ethanol intake for at least about 12–24 hours, most preferably for at least about 48 hours.

The invention will be further described by reference to the following detailed examples, wherein melting points were determined in open capillary tubes on a Thomas-Hoover apparatus and are uncorrected. Elemental analyses were performed by M-W-H Laboratories, Phoenix, Ariz. Magnetic resonance spectra were obtained on IBM-Bruker AC-300 (300 MHz, ¹H NMR; 75 MHz, ¹³C NMR) and IBM-Bruker AC-200 (200 MHz, ¹H NMR; 50 MHz, ¹³C NMR) spectrometers, and chemical shifts are reported as δ values (ppm) relative to TMS. IR spectra were recorded on a Nicollet 5DXC FT-IR spectrometer, and peak position are expressed in cm⁻¹. Mass spectra were obtained on AEI MS 30, Finnigan 4000 Cl, and VG 70, 70 EHF instruments. All TLC data were determined with E. Merck Art. 5554 DC-Alufolien Kieselgel 60 $F_{254}$. Column chromatography was carried out on E. Merck silica gel 60 (230–400 mesh). Reagents were purified according to known procedures.

Naltrexone was obtained from Mallinckrodt. DADLE, DAMGO and DPDPE were obtained from Bachem, Inc., Torrance, Calif. DSLET was obtained from Serva Biochemicals, Westbury, N.Y.

EXAMPLE I

7-Benzylidene-7-dehydronaltrexone (I, $R^1$=cyclopropylmethyl, $R^2$=OH, $R^3$=$R^4$=$R^5$=H).

To a stirred solution of naltrexone hydrochloride (200 mg, 0.53 mmol) in MeOH (8 ml) were added sodium hydroxide (1 N, 4 ml) and benzaldehyde (0.5 ml, 3.7 mmol) in an ice bath. The mixture was refrigerated for 14 hr. The mixture was neutralized with 1 N aqueous HCl and extracted with $CHCl_3$(3X). The combined organic layers were washed with brine, dried, and concentrated to afford a crude product which was purified on a Sephadex Column (CH-20, MeOH) to give 7-benzylidene-7-dehydronaltrexone (113 mg, 50%): mp 230° C. dec; $R_f$0.60 ($CHCl_3$-MeOH-acetone, 19:0.5:0.1); IR (liquid film, $cm^{-1}$) 1685, 1611; $^1$H NMR ($CDCl_3$, 300 MHz) δ 0.12–0.15 (m, 2H), 0.52–0.58 (m, 2H), 0.79–0.90 (m, 1H), 1.64 (d, J=11.9 Hz, 1H), 2.22–2.50 (m, 6H), 2.63–2.77 (m, 2H), 3.01 (d, J=15.3 Hz, 1H), 3.13 (d, J=18.6 Hz, 1H), 3.21 (d, J=6.2 Hz, 1H), 4.72 (s, 1H), 6.63 (d, J=8.1 Hz, 1H), 6.75 (d, J=8.1 Hz, 1H), 9.85 (m, 5H); MS m/e 429 ($M^+$, EI). Hydrochloride salt: $R_f$0.72 (butanol-acetone-$H_2O$, 2:1:1); mp 210° C. dec. Anal. ($C_{27}H_{27}O_4N$·HCl) C, H, N. Cl.

EXAMPLE II

Evaluation of Antagonist Activity of 7-Benzylidene-7-dehydronaltrexone.

A. Smooth Muscle Assays

1. Guinea Pig Ileal Longitudinal Muscle (GPI).

Ilea from guinea pigs were taken approximately 10 cm from the ileocecal junction, and a strip of longitudinal muscle with the myenteric plexus attached was prepared by method of H. P. Rang *Brit. J. Pharmacol.*, 22, 356 (1964). A 1 cm portion of this strip was then mounted between two platinum electrodes placed in a 10 ml organ bath and connected to an isometric transducer; contractions were recorded on a polygraph. Contractions of the ileal strip were initiated by supramaximal rectangular pulses in all preparations (80 V of 0.5 ms duration at a frequency of 0.1 Hz). Krebs bicarbonate solution containing 1.25 μM chlorpheniramine maleate was the bathing solution and was continuously bubbled with 95% $O_2$ and 5% $CO_2$. The organ bath was maintained at 36°–37° C. The longitudinal muscle strip was allowed to equilibrate with continuous stimulation for a minimum of 90 min. Cumulative concentration-response curves were determined after drugs were added to the bath in 10- to 50-μl amounts and washed out with two 10 ml portions of buffer after noting their maximum effects.

2. Mouse Vas Deferens (MVD).

This assay was performed according to the description by G. Henderson et al., *Brit. J. Pharmacol.*, 46, 764 (1972). Both vasa deferentia were dissected out of mice and mounted singly through two platinum ring electrodes in a 10 ml organ bath. The bath contained Krebs bicarbonate solution that was continuously bubbled with 95% $O_2$ and 5% $CO_2$. The organ bath was maintained at 37° C. The tissue was attached to an isometric transducer and stimulated transmurally with rectangular pulses (0.1 Mz, 1 ms duration, supramaximal voltage). Drugs were added cumulatively to the bath in 10- to 50-μl amounts and washed out after noting their maximum effect.

B. Pharmacology

The antagonist potency of the compound of Example I (BNTX) was compared to the activity of NTI and naltrexone in vitro on the mouse vas deferens (MVD) and guinea pig ileum (GPI) preparations. Each compound (100 nM) was incubated for 15 min with the tissue prior to adding graded doses of a standard agonist for determination of an $IC_{50}$ value. The standard agonists employed were [D-Ala$^2$, D-Leu$^5$]enkephalin (DADLE), morphine (M), and ethylketazocine (EK); these are selective for delta (DADLE), mu (M) and kappa (EK) opioid receptors. Concentration-response curves were obtained in the absence (control) and the presence of the antagonist are expressed as $IC_{50}$ values. The $IC_{50}$ ratio represents the $IC_{50}$ in the presence of the antagonist divided by the control $IC_{50}$ value in the same tissue. Therefore, a high $IC_{50}$ ratio represents a correspondingly high degree of antagonism at a particular receptor. This $IC_{50}$ ratio was employed to calculate the Ke value using the equation Ke=[antagonist]/($IC_{50}$ ratio-1). Therefore, a low Ke represents a correspondingly high degree of binding at a particular receptor. The results of these bioassays are summarized on Table II, below.

TABLE II

COMPARISON OF OPIOID ANTAGONIST POTENCIES IN THE GPI AND MVD PREPARATIONS

| Antagonist | Ke, nM | | | Ke Ratio | |
| --- | --- | --- | --- | --- | --- |
| | δ$^a$ | μ$^b$ | κ$^b$ | μ/δ | κ/δ |
| 7-Benzylidene-7-dehydronaltrexone (BNTX) | 2.9 | 8.3 | 100 | 2.9 | 35 |
| NTI$^c$ | 0.13 | 29 | 46 | 223 | 345 |
| Naltrexone | 24 | 1.0 | 5.5 | 0.03 | 0.17 |

$^a$Assayed in the MVD using DADLE as agonist.
$^b$Assayed in the GPI using morphine (μ) and ethylketazocine as agonists.
$^c$δ-selective antagonist (J. Med. Chem., 31, 281 (1988)).

The data shown in Table II indicate that BNTX is a δ-selective antagonist. It can be noted that its Ke ratios are less than those of the standard δ agonist NTI, but greater than those of naltrexone, a μ-selective antagonist.

While the smooth muscle pharmacological data presented on Table II (δ in MVD; μ and κ in GPI) reveal that BNTX is δ-selective, the data do not identify its δ subtype selectivity, if any, because it is likely that the MVD preparation contains a different δ subtype or mixture of δ subtypes as compared to the brain.

Therefore, a better assessment of the δ subtype selectivity can be obtained from binding of brain membranes and from antagonism studies in mice. The binding of BNTX to guinea pig brain membranes was determined using the general method of L. L. Werling et al., *J. Pharmacol. Exp. Ther.*, 233, 722 (1985), as modified by A. E. Takemori et al., *J. Pharmacol. Exp. Ther.*, 246, 255 (1988). The radio-ligands employed were [$^3$H]DPDPE ([D-Pen$^2$, D-Pen$^5$] enkephalin) for δ$_1$ receptors, [$^3$H]DSLET([D-Ser$^2$-Leu$^5$]enkephalin-Thr$^6$) for δ$^2$ receptors, [3H]DAMGO for μ receptors and U69593(trans-(+)-3,4-dichloro-N-methyl-N-[2-(1-pyrididinyl)cyclohexyl]benzeneacetamide) for κ receptors.

As shown by the data on Table III, below, BNTX exhibited a binding ratio, Ki (δ$_2$)/Ki(δ$_1$) of about 100. Since a high Ki value at a given receptor indicates a lower binding affinity for that receptor, it can be seen that BNTX is highly selective for δ$_1$ receptor sites.

TABLE III

BNTX RECEPTOR SELECTIVITY DATA

| Standard Antagonist | Selectivity | Smooth Muscle Ke, nM | Binding Ki, nM | ED$_{50}$ Ratio[a] ("Potency Ratio") |
|---|---|---|---|---|
| DADLE | $\delta_1$ | 2.9 | — | — |
| DPDPE | $\delta_1$ | 5.2 | 0.1 | 7.2 |
| DSLET | $\delta_2$ | 2.1 | 10.8 | 0.91 |
| Morphine | $\mu$ | 8.3 | — | — |
| DAMGO | $\mu$ | — | 13.3 | 0.88 |
| EK | $\kappa$ | 100 | | |
| U50488H | $\kappa$ | — | 59 | 1.2 |

[a]ED$_{50}$ of agonist in presence of BNTX/ED$_{50}$ of agonist.

The antagonist effect of BNTX on antinociception was evaluated in mice using the tail flick assay, in accord with the procedure of A. E. Takemor, et al., *J. Pharmacol. Exp. Ther.*, 243, 91 (1987). At least three groups of ten mice were used to generate dose-response curves. A mouse was regarded as positive for antinociception if the latency to flick its tail was more than the control latency plus 3 S.D. of the mean reaction time of the group. The reaction times were determined at the peak time for antinociception after administration of various agonists. Intra-cerebroventricular (i.c.v.) injections were made in a volume of 5 μl by the method of T. J. Haley et al., *Br. J. Pharmacol.*, 12, 12 (1957).

On Table III, the potencies are expressed as ED$_{50}$ ratios, which represent the ED$_{50}$ of the standard agonist administered subcutaneously in the presence of BNTX (6.25 pmoL/i.c.v./mouse), divided by the ED$_{50}$ of the standard agonist. Thus, the dose-response curve obtained for DPDPE was shifted by a factor of about 7.2 to higher concentration, while the curves of DSLET, morphine and U50488H (κ agonist) were not shifted significantly. Therefore, the binding data determined on guinea pig brain membranes, correlate with the in vivo data, and are superior to the smooth muscle-based assays data shown on Table II, as an indicator of δ subtype selectivity. It is believed that BNTX is the first $\delta_1$ opioid receptor subset-selective antagonist to be identified.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed is:

1. A method for blocking δ-opioid receptors in mammalian tissue comprising contacting said receptors with an amount of a compound of the formula:

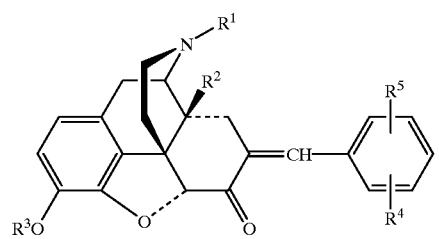

(I)

wherein R$^1$ is (C$_1$–C$_5$)alkyl, C$_3$–C$_6$(cycloalkyl)alkyl, C$_5$–C$_7$(cycloalkenyl)alkyl, (C$_6$–C$_{10}$)aryl, (C$_6$–C$_{10}$aryl (C$_1$–C$_5$)alkyl, trans(C$_4$–C$_5$)alkenyl, allyl or furan-2-ylalkyl; R$^2$ is H, OH or O$_2$C(C$_1$–C$_5$)alkyl; R$^3$ is H, (C$_1$–C$_5$)alkyl, or ((C$_1$–C$_5$)alkyl)C=O; and R$^4$ and R$^5$ are individually H, F, Cl, Br, NH$_2$, NO$_2$, (C$_1$–C$_5$)alkyl or (C$_1$–C$_5$)alkoxy, or R$^4$ and R$^5$ together are benzo or dioxymethylene; and the pharmaceutically acceptable salts thereof, wherein the amount is effective to block δ-opioid receptors in said tissue.

* * * * *

UNITED STATES PATENT AND TRADEMARK OFFICE
CERTIFICATE OF CORRECTION

PATENT NO. : 6,271,239 B1
DATED : August 7, 2001
INVENTOR(S) : Philip S. Portoghese It is certified that error appears in the above-identified patent and that said Letters Patent is hereby corrected as shown below:

Column 1,
Lines 5-8, delete "This is a division, of application Serial No. 08/267,844, filed on June 29, 1994, now abandoned which is a continuation of application Ser. No. 07/867,997, filed Apr. 13, 1992 now abandoned." and insert -- This is a division of application Serial No. 07/867,997, filed on April 13, 1992, now abandoned which is a continuation of application Ser. No. 08/267,844, filed June. 29, 1994 now abandoned. --, therefor.

Column 7,
Line 26, delete "N." between "H," and "C1." and insert -- N, --, therefor.
Line 36, delete "P." between "H." and "Rang" and insert -- B. --, therefor.

Column 8,
Line 45, delete "do" after "data" and insert -- does --, therefor.

Column 10,
Line 14, insert -- which comprises said receptors, said method -- after "tissue".

Signed and Sealed this

Twenty-first Day of May, 2002

Attest:

Attesting Officer

JAMES E. ROGAN
Director of the United States Patent and Trademark Office